(12) United States Patent
Plochocka et al.

(10) Patent No.: US 6,706,817 B2
(45) Date of Patent: Mar. 16, 2004

(54) POLYMERIC HYDROGELS

(75) Inventors: Krystyna Plochocka, Scotch Plains, NJ (US); Jeffrey A. Lynn, West Milford, NJ (US)

(73) Assignee: ISP Investments Inc., Wilmington, DE (US)

( * ) Notice: Subject to any disclaimer, the term of this patent is extended or adjusted under 35 U.S.C. 154(b) by 18 days.

(21) Appl. No.: 10/397,900

(22) Filed: Mar. 26, 2003

(65) Prior Publication Data

US 2003/0236349 A1 Dec. 25, 2003

Related U.S. Application Data

(62) Division of application No. 10/177,995, filed on Jun. 21, 2002, now Pat. No. 6,583,225.

(51) Int. Cl.[7] .............................. C08F 8/00; C08F 25/02; C08F 261/04
(52) U.S. Cl. ........................ 525/193; 525/191; 525/252; 525/253
(58) Field of Search ................................. 525/191, 193, 525/252, 253

Primary Examiner—James J. Seidleck
Assistant Examiner—Thao Tran
(74) Attorney, Agent, or Firm—Walter Katz; William J. Davis; Marilyn J. Maue

(57) ABSTRACT

What is described is a polymeric hydrogel of a polymeric anhydride or acid, e.g. maleic anhydride or maleic acid polymer, or copolymer thereof, crosslinked with a crosslinking agent containing at least 2 crosslinkable groups, particularly, —OH or —$NH_2$, or both. The reaction product is a crosslinked polymeric ester or amide/imide, or both, suitably having a mole ratio of —OH, or —$NH_2$, to —COOH, of 1:10 to 10:1, preferably 2:10 to 7:1. The hydrogel is particularly swellable in water, e.g. >100% in 1 hour in aqueous media; and forms a thin, tacky layer on a substrate, which property is useful in bioadhesive products.

5 Claims, 4 Drawing Sheets

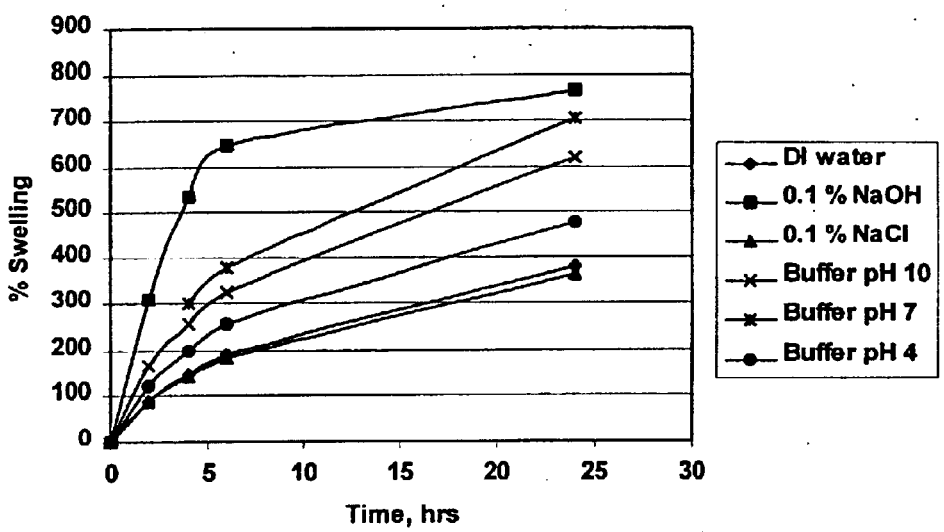
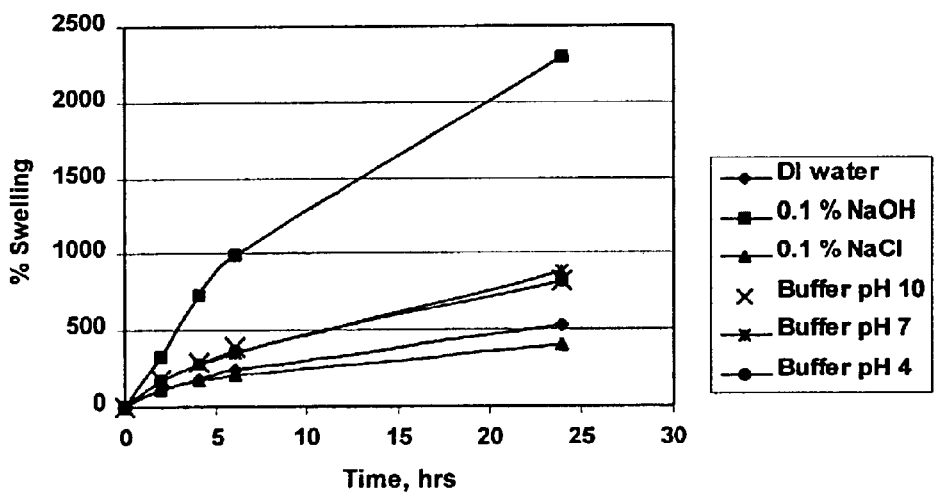

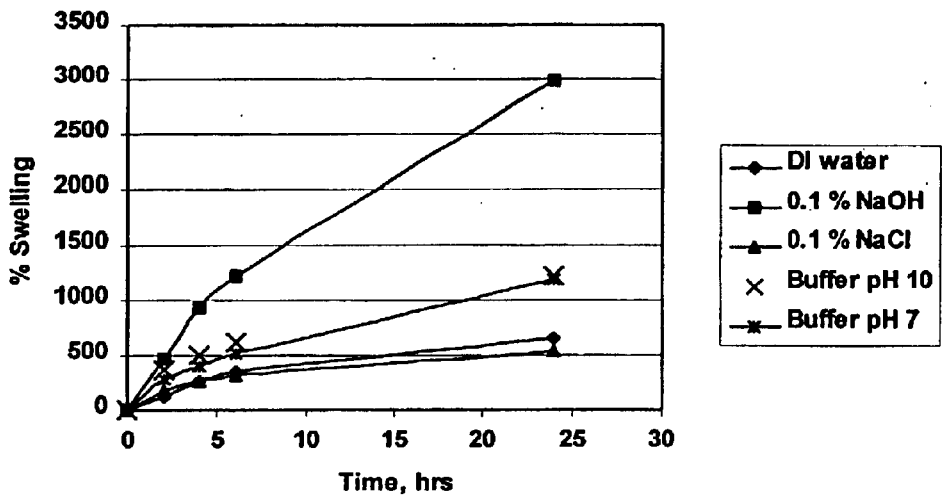
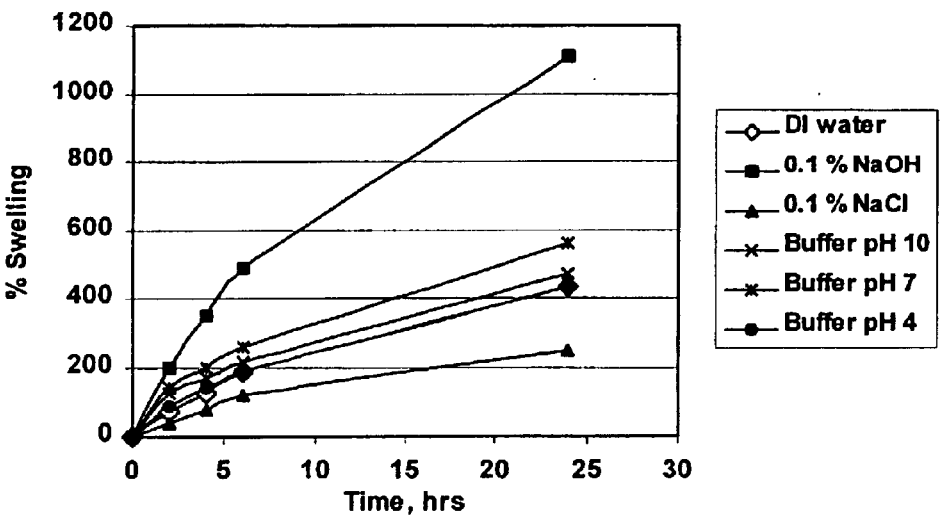

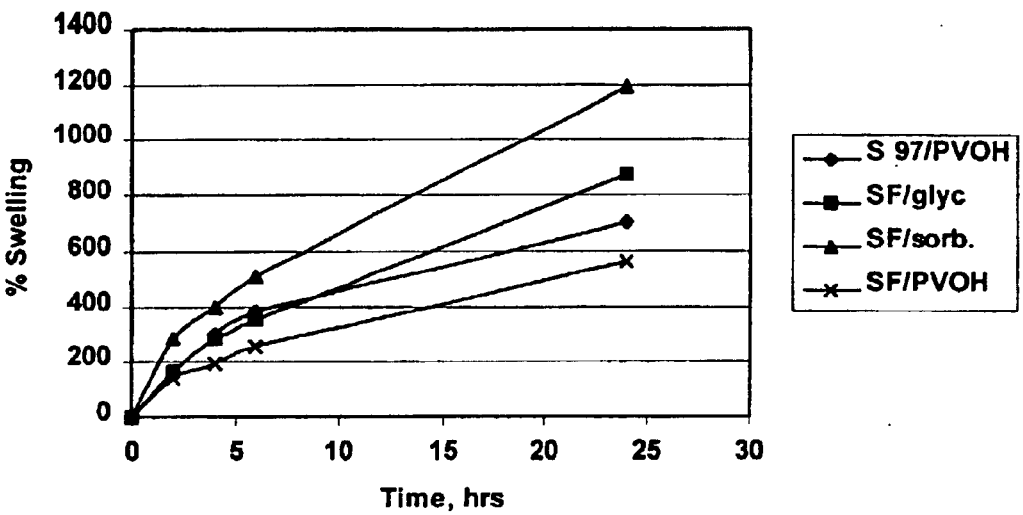
Figure 5. Swelling versus time in buffer pH 7. Different crosslinkers.
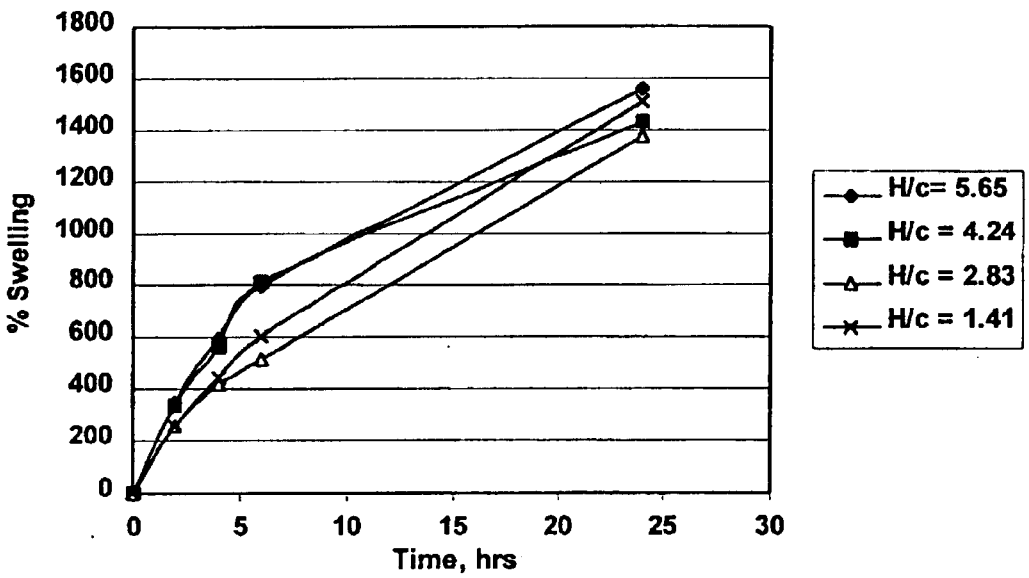
Figure 6. Swelling of S 97/glycerol hydrogels in buffer pH 7. Differing -OH/-COOH (H/c) ratios

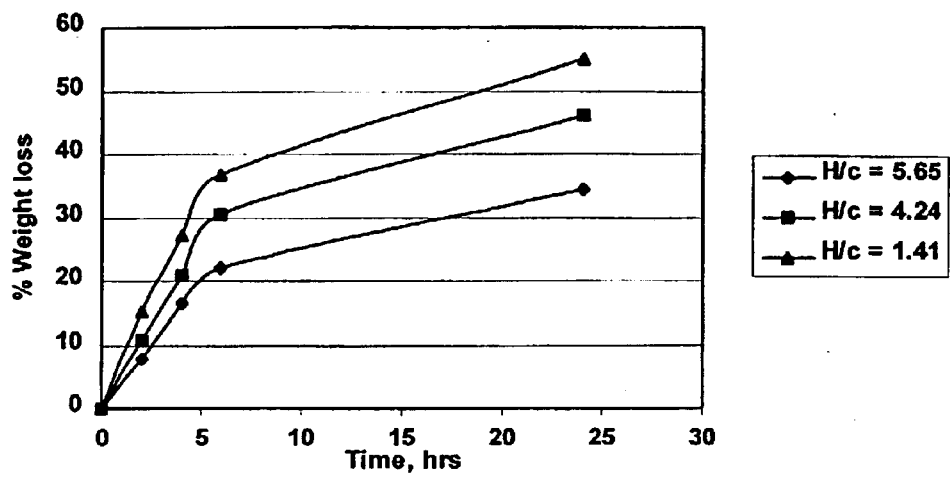

POLYMERIC HYDROGELS

This application is a Division of No. 10/177,995 filed Jun. 21, 2002 now U.S. Pat No. 6,583,225.

BACKGROUND OF THE INVENTION

1. Field of the Invention

This invention relates to hydrogels, and, more particularly, to polymeric hydrogels which are crosslinked polymeric esters or amides/imides, or both, of a polymeric anhydride or acid, or copolymers thereof, which are very swellable in water, and form thin, tacky layers on a substrate, and bioadhesive products thereof.

2. Description of the Prior Art

Hydrogels are polymeric materials which can swell appreciably in water. However, what is described as hydrogels can be viscous polymeric solutions without the swelling characteristic of a true hydrogel. Such hydrogels also are not tacky, a necessary property for making bioadhesive products. See U.S. Pat. Nos. 4,740,365; 4,990,551; 5,135,753; 5,336,501; and 5,846,214. Accordingly, it is desired to provide new and useful polymeric hydrogels having exceptional swelling properties in water, and which are tacky; and bioadhesive products of such hydrogels.

IN THE DRAWINGS

FIG. 1 Swelling of Gantrez AN 200 SF/PVOH hydrogel.

FIG. 2 Swelling of Gantrez S 97/glycerol hydrogel.

FIG. 3 Swelling of Gantrez S 97/sorbitol hydrogel.

FIG. 4 Swelling of Gantrez S 97/PVOH hydrogel.

FIG. 5 Swelling versus time in buffer pH 7.

FIG. 6 Swelling of S 97/Glycerol hydrogels in buffer pH 7.

FIG. 7 Weight loss at room temperature for S 97/glycerol hydrogels.

SUMMARY OF THE INVENTION

What is described herein is a polymeric hydrogel which is a polymeric anhydride or acid or copolymer thereof, e.g. maleic anhydride or maleic acid polymer, or copolymer thereof, preferably with an alkylvinylether; e.g. methylvinylether or isobutylvinylether; or an olefin, e.g. butylenes or isobutylene; crosslinked with a crosslinking agent having at least 2 crosslinkable groups; e.g. an alcohol, —OH, an amine, —NH$_2$, or alcohol-amine groups, e.g. polyols such as polyvinyl alcohol, glycerol, glucose, sorbitol, pentaerithyritol, nonionic surfactants, alginates, starch, cellulose, ethylene glycol, diethylene glycol and ethoxylated/propoxylated derivatives thereof; or a polyamine or ethoxylated amine, e.g. an aminoalcohol, amino acid and the like.

The polymeric hydrogel of the invention preferably has a mole ratio of —OH or —NH$_2$:COOH of 1:10 to 10:1, most preferably 2:10 to 7:1.

The polymeric hydrogel herein is particularly characterized by its exceptional swelling properties and tackiness, which are useful for making bioadhesive products.

The polymeric hydrogels of the invention are made by reacting a maleic anhydride or maleic acid polymer, or copolymer, with a crosslinking agent having at least 2 crosslinkable groups, particularly a polyol or polyamine, or alcohol amine, unexpectedly, in water as solvent, in the presence of an esterification or amidation catalyst.

The reaction product is a crosslinked polymeric ester or amide/imide, or both.

Generally the polymer hydrogels of the invention contain a considerable amount of water, usually about 50 wt % or more.

DETAILED DESCRIPTION OF THE INVENTION

The polymeric hydrogel of the invention is made by a crosslinking reaction between an acidic polymer, particularly copolymers of maleic anhydride or maleic acid, or mixtures thereof, and a comonomer, e.g. an alkylvinylether, such as methylvinylether or isobutylvinylether, or olefin, e.g. butylenes or isobutylene; with a suitable crosslinking agent, i.e. a compound having at least 2 groups crosslinkable with such copolymers, such as present in polyols, diols, triols, etc. present in compounds such as glycerol, pentaerithyritol, sorbitol, and nonionic surfactants;, in polymers such as polyvinyl alcohol, (PVOH), sugars, e.g. glucose, saccarose, alginates, starch, cellulose, and its derivatives; or amines, or aminoalcohols, present and in polyamines, polyaminoalcohols, ethoxylated amines, amino acids, e.g. arginine, glutamine, lysine and gelatine.

The crosslinking reaction produces a crosslinked polymeric ester or amide/imide, or mixed ester-amide/imide. Unexpectedly this reaction suitably is carried out in an aqueous solution or slurry of polymer and crosslinking agent in the presence of an esterification or amidization catalyst, e.g. sulfuric acid, phosphoric acid or toluene sulfonic acid, at about 60–130° C., preferably 80–110° C.

Preferably the hydrogel is formed as continuous molds or sheets on a substrate, not as discrete particles in the bulk.

The polymeric hydrogel obtained has advantageous swelling properties in various solvent media e.g. water, base, salt, buffers, etc. When applied to a substrate, the polymeric hydrogel of the invention forms a thin, tacky layer suitable for use as a bioadhesive. The hydrogels also are useful in oral care, personal care, wound care and drug delivery systems.

The physical properties of the hydrogel, e.g. swelling/tack/solubility/rate of drying/dispersibility in water, and viscoelastc properties, and feel, etc. can be predetermined by the mole ratio of —OH or —NH$_2$:COOH in the hydrogel, as well as the reaction conditions employed, e.g. temperature, catalyst, reaction time, amount of water, etc.

Preferably the mole ratio of —OH or —NH$_2$:COOH in the hydrogel is 1:10 to 10:1, most preferably 2:10 to 7:1.

The invention will now be described in specific detail by the following examples.

EXAMPLE 1

Maleic anhydride/methylvinylether copolymer (MAN) (Gantrez® AN SF i.e. solvent free anhydride) powder (20 g) was slurried into 188 g of aqueous polyvinyl alcohol (PVOH) solution containing 20 wt % PVOH. The mole ratio of —OH groups in the PVOH to the —COOH groups in Gantrez® AN was 3.34. Then 2 g of p-toluenesulfonic acid was added to the slurry with agitation. The agitated slurry was poured into a section of flexible Tygon tubing which was sealed by clamping at both ends. The tubing served as a mold for making a rod-shaped pieces of hydrogel. The tubing with slurry inside then was placed in a 105° C. oven and it was held at that temperature for 6 hrs. After cooling to room temperature, a rod-shaped, rubbery, slightly tacky, uniform, semi-transparent hydrogel was obtained. The tubing was cut into sections for swell testing in various media.

The sections of hydrogel were weighted and placed in DI water, buffered at pH levels of 4, 7 and 10, and in 0.1% NaOH and 0.1% NaCl aqueous solutions. The pieces were taken out, wiped dry and weighed again. The pieces retained their shape and integrity after soaking for 6 weeks.

EXAMPLE 2

Maleic acid/methylvinylether (MAA) (Gantrez® S-97, 16.78% by wt in water) (120 g) was blended with 200 9 PVOH (20% in water) and 4 g of sulfuric acid (50%) to yield a viscous solution. The mole ratio of —OH groups from PVOH to —COOH groups from Gantrez® S-97 was 3.95. The solution was poured into Tygon tubing and kept in a 105° C. oven for 6 hrs. After cooling the tubing was removed to provide a rod-shaped, slightly tacky, uniform, transparent hydrogel, which was tested as in Example 1.

EXAMPLE 3

Gantrez® S-97 (16.78% by wt in water) 240 g, glycerol 80 g and 8 g sulfuric acid (50%) were blended to yield a uniform solution. The mole ratio of —OH groups from glycerol to —COOH groups from Gantrez S-97 was 5.65. The solution was poured into several 8 oz jars to form about 10 mm thick layer. The jars were sealed and placed in a 105° C. oven for 9 hrs. After cooling to room temperature, a flat, soft, smooth, colorless, transparent hydrogel molds were obtained. The hydrogels were very tacky, attached themselves lightly to skin, but could be easily removed without leaving any residue. Pieces cut from the molds were tested for swelling as described in the preceding examples. The tackiness vs. % swelling curves showed a diminishing relationship. After reaching 300 to 500% of swelling, the hydrogels became non-tacky.

EXAMPLE 4

Hydrogel molds were prepared as in Example 3; however, starting with a blend of Gantrez® S-97 120 g, sorbitol (70% aq.) 116 g and sulfuric acid (50%) 8 g. The mole ratio of —OH groups from sorbitol to —COOH groups from Gantrez S-97 was 5.8. The hydrogels obtained had an appearance, feel and swelling behavior very similar to those made with glycerol, and their tack behavior was also similar.

EXAMPLE 5

Blends of Gantrez® S-97 and glycerol, or sorbitol, or PVOH, as in Examples 2 through 4 containing sulfuric acid as a catalyst, were poured onto a polyester cloth placed at the bottom of glass trays to a thickness of about 3 mm. Then the trays were covered with a plastic wrap and placed in a 85° C. oven for 6 hrs, and, thereafter, in a 105° C. oven for 9 hrs. After cooling to room temperature, the products were recovered as tacky transparent thin sheets on the polyester backing. Tackiness was compared by touch:

TABLE 1

Tack of Thin Layer Hydrogels as Evaluated by Touch

| Crosslinker | Tack |
|---|---|
| Glycerol | Very tacky |
| Sorbitol | Very tacky |
| PVOH | Slightly tacky |
| Band Aid ® (J&J) | Very tacky |
| Scotch ® tape | Tacky |

EXAMPLE 6

A blend of Gantrez® S-97 (16.7.8% in water) 120 g, ethanolamine 14 g and p-toluenesufonic acid 2 g, is molded in glass jars as in Example 3. The mole ratio of —OH or —NH$_2$ groups from ethanolamine to —COOH groups from Gantrez® S-97 is 2.0. Hydrogels recovered after molding have an appearance and feel similar to the products of Examples 3 and 4.

FIGS. 1–7 show the swelling characteristics of the hydrogels of the present invention in various aqueous media in graphical representation. In general, the swelling property and tack of the hydrogel product of the invention is predetermined by the following factors: (1) the particular crosslinker used, (2) the —OH or —NH$_2$/—COOH mole ratio, and (3) the aqueous solvent media used in its preparation. Usually, the order of swelling for a given crosslinker used, in a pH 7 buffer, was sorbitol>glycerol>PVA; with swelling ranging from 200% to 1200% over a soaking time of 1–25 hours; and in different solvent media it was 0.1% NaOH>>pH 7≧pH 10≧pH 4 >DI water ~0.1% NaCl: ranging from 100% to 3000% for a similar soaking period.

The hydrogels with glycerol and sorbitol were very tacky at time zero, but, after swelling to >300%, they became only slightly tacky, and then were non-tacky at >500% swelling; PVA crosslinked hydrogels were slightly tacky at time zero. A significant degree of swelling without loss of integrity is indicative of a crosslinked hydrogel.

Hydrogels with PVA as crosslinker retained their shape after soaking in water for several weeks.

The bioadhesive hydrogels of the invention find wide application in many products, such as topical drug and cosmetic delivery systems; e g. skin and mucous membranes; personal care products such as skin care; an oral care, e.g. denture liners, flavor and drug delivery; wound care and in systems for drug delivery.

While the invention has been described with particular reference to certain embodiments thereof, it will be understood that changes and modifications may be made which are within the skill of the art Accordingly, it is intended to be bound only by the following claims, in which:

What is claimed is:

1. A method of making a polymeric hydrogel comprising an anhydride or acid-polymer, maleic anhydride or maleic acid polymer, or copolymer thereof with an alkylvinylether or olefin, or copolymer thereof, crosslinked with a crosslinking agent having at least 2 crosslinkable groups, where the crosslinkable group is selected from the group consisting Of an alcohol (—OH), amine (—NH$_2$) or alcohol-amine (—OH) (—NH$_2$), and water, which method comprises reacting a maleic anhydride or maleic acid polymer with a crosslinking agent having at least 2 crosslinkable groups in the presence of an esterification or amidation catalyst, in water as solvent.

2. A method according to claim 1 wherein said crosslinking agent is an alcohol, amine or alcohol-amine.

3. A method according to claim 1 which is run at 60–130° C.

4. A method according to claim 3 which is run at 80–110° C.

5. The reaction product of claim 1 which is a crosslinked polymeric ester or amide/imide, or both.

* * * * *